(12) United States Patent
Meinzinger et al.

(10) Patent No.: US 8,114,249 B2
(45) Date of Patent: Feb. 14, 2012

(54) METHOD AND APPARATUS FOR MONITORING AN EVAPORATOR

(75) Inventors: Rupert Meinzinger, Kirchroth (DE); Manfred Ziegler, Ruderting (DE)

(73) Assignee: Krones AG, Neutraubling (DE)

( * ) Notice: Subject to any disclaimer, the term of this patent is extended or adjusted under 35 U.S.C. 154(b) by 764 days.

(21) Appl. No.: 11/994,146

(22) PCT Filed: Jun. 28, 2006

(86) PCT No.: PCT/EP2006/006226
§ 371 (c)(1),
(2), (4) Date: Oct. 28, 2008

(87) PCT Pub. No.: WO2007/003313
PCT Pub. Date: Jan. 11, 2007

(65) Prior Publication Data
US 2009/0126518 A1   May 21, 2009

(30) Foreign Application Priority Data

Jul. 1, 2005   (DE) .......................... 10 2005 030 822

(51) Int. Cl.
*B01D 1/16* (2006.01)
*A61L 2/24* (2006.01)
*F22B 1/28* (2006.01)
*G01N 25/00* (2006.01)

(52) U.S. Cl. ............ 159/44; 73/865.9; 159/3; 159/48.1; 422/299; 422/307; 422/528; 374/45; 392/386; 392/387

(58) Field of Classification Search ................ 159/3, 44, 159/48.1; 73/863.11, 865.9; 422/299, 305, 422/307, 528; 392/386, 387; 374/45
See application file for complete search history.

(56) References Cited

U.S. PATENT DOCUMENTS

| | | | |
|---|---|---|---|
| 3,544,004 A * | 12/1970 | Kitanosono et al. | ........ 236/15 R |
| 3,949,565 A * | 4/1976 | Roop | .............. 62/50.2 |
| 5,078,976 A | 1/1992 | Shibauchi et al. | |
| 5,290,511 A | 3/1994 | Newman et al. | |
| 5,304,286 A * | 4/1994 | Palmer | .......... 202/167 |
| 5,580,607 A | 12/1996 | Takekuma et al. | |
| 5,879,648 A | 3/1999 | Hada et al. | |
| 6,140,615 A * | 10/2000 | Matsumoto | ............. 219/441 |
| 6,480,257 B2 * | 11/2002 | Cassidy et al. | ................ 392/470 |
| 2004/0182855 A1 | 9/2004 | Centanni | |
| 2006/0032248 A1* | 2/2006 | Kates | .............. 62/129 |
| 2008/0190298 A1* | 8/2008 | Morgandi | ....... 99/282 |

FOREIGN PATENT DOCUMENTS

| | | |
|---|---|---|
| DE | 2406050 | 9/1974 |
| DE | 3728595 | 3/1989 |
| DE | 3888809 | 6/1989 |
| DE | 197 04 639 A1 | 8/1998 |
| DE | 19704639 | 8/1998 |
| DE | 60102090 | 12/2004 |
| EP | 0321908 | 6/1989 |
| JP | 4361754 | 12/1992 |
| WO | WO-9007366 | 7/1990 |
| WO | WO 98/31844 | 7/1998 |
| WO | WO-9831844 | 7/1998 |
| WO | WO 03/082355 A1 | 10/2003 |
| WO | WO-03082355 | 10/2003 |

* cited by examiner

*Primary Examiner* — Virginia Manoharan
(74) *Attorney, Agent, or Firm* — Marshall, Gerstein & Borun LLP

(57) ABSTRACT

A method and an apparatus for monitoring an evaporator (2), whereby a liquid is applied onto a heating unit (3) and evaporated and the temperature drop caused by the evaporation heat in the heating unit (3) is detected. In the absence of a predetermined temperature drop, a signal is generated. In this way, the evaporation process can be controlled in a simple manner.

2 Claims, 1 Drawing Sheet

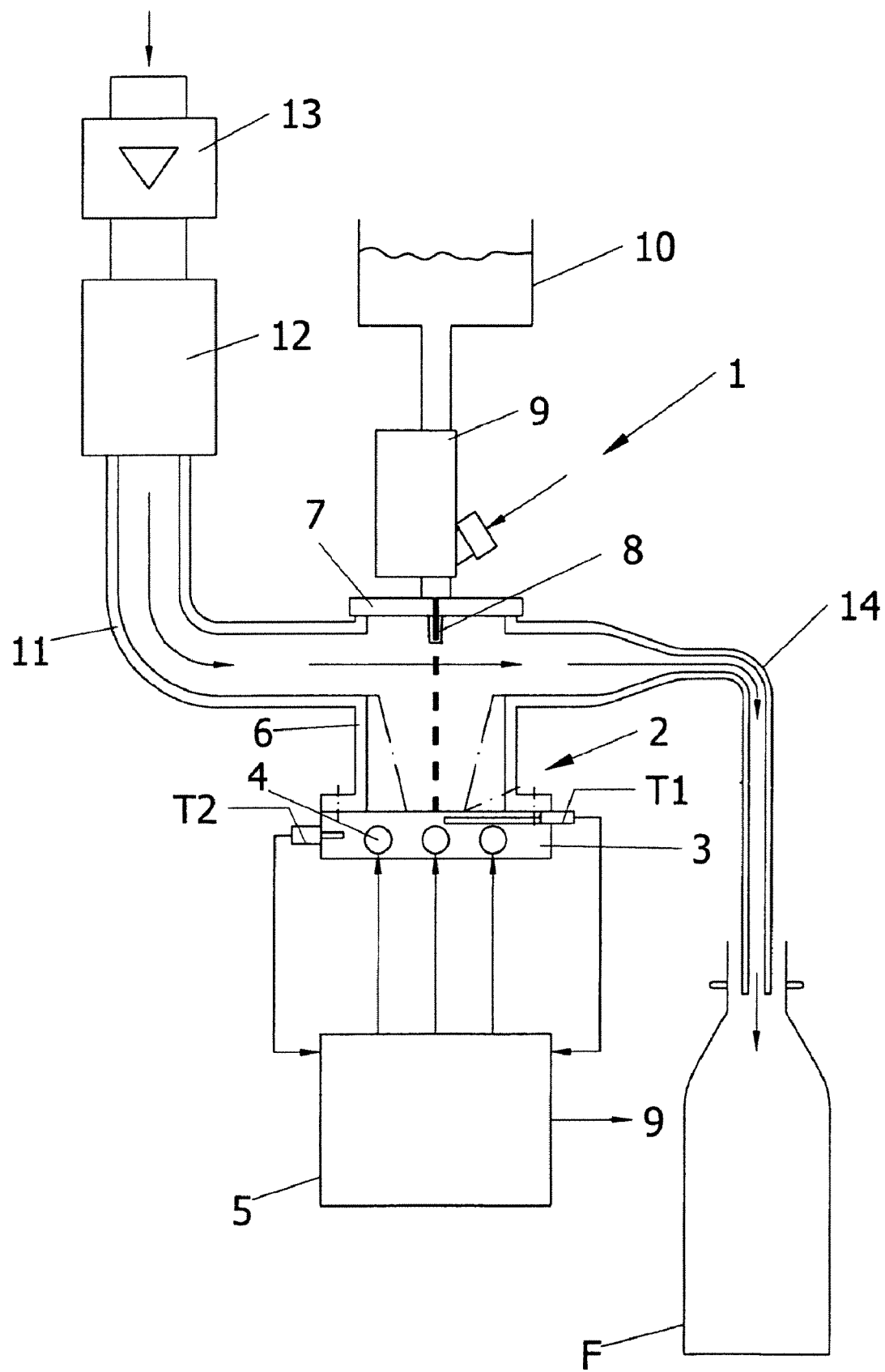

METHOD AND APPARATUS FOR MONITORING AN EVAPORATOR

CROSS-REFERENCE TO RELATED APPLICATION

The present application claims the benefit of priority of International Patent Application No. PCT/EP2006/006226 filed on Jun. 28, 2006, which application claims priority of German Patent Application No. 10 2005 030 822.8 filed Jul. 1, 2005. The entire text of the priority application is incorporated herein by reference in its entirety.

The disclosure pertains to a method for monitoring an evaporator, in particular for a disinfection liquid for sterilizing containers, as well as an apparatus for the implementation thereof.

BACKGROUND

It is known in the art to evaporate disinfection liquids, for example hydrogen peroxide, to a greater or lesser extent by means of a metered application onto a heating unit and to supply the vapor produced in this manner to the sterilizing containers, for example bottles or cups, if necessary after mixing it with hot air (DE 37 28 595 A1, U.S. Pat. No. 5,879,648).

It is further known in the art to capture the temperature of a heating unit for evaporating liquids by means of sensors and to control the heating elements of the heating unit, for example electric heating cartridges, in this manner (WO 90/07366, DE 197 04 639 A1). Although maintaining the desired temperature of the heating unit is improved in this manner, it is not possible to determine whether the predetermined amount of liquid was indeed supplied and evaporated. This is particularly disadvantageous if the vapor is used for sterilizing containers for food products since requirements in this area are strict and range from an exact control of the sterilization process to keeping records of all pertinent readings for every single container.

It has also been proposed to measure values such as temperature, humidity, vapor concentration, flow or pressure by means of sensors arranged in a sterilization chamber for containers attached to an evaporator (EP 1 368 086 B1). Such monitoring is very complex and costly and of limited informative value with regard to the amount of evaporated sterilization agent.

SUMMARY OF THE DISCLOSURE

The disclosure is based on the task of providing a method for monitoring an evaporator of the type mentioned in the beginning hereof which is easy to execute and allows for a direct control over the evaporated liquid. In addition, a cost-efficient and reliable apparatus for implementing the method is to be provided.

The control according to the disclosure of the evaporation heat drawn away from the heating unit by the impacting liquid is a simple and reliable means of recognizing interferences both in the supply of liquid, for example due to clogged nozzles or valves, and in the evaporation process, for example due to inaccurate dropping or unclean surfaces. It has been shown, quite surprisingly, that when even a few milliliters of liquid, for example hydrogen peroxide in aqueous solution, are applied onto a heating unit with a temperature of, for example, 180° C., its temperature drops quite abruptly to, for example, 160° C.; such a drop in temperature can be easily registered by means of conventional temperature sensors.

A particularly exact capturing of the temperature drop is possible if according to a further embodiment of the disclosure the temperature of the heating unit is measured in the area where the liquid is applied.

A further increase of precision is possible if according to a further embodiment of the disclosure the temperature of the heating unit is also measured outside of the liquid application area and correlated with the temperature inside the liquid application area. In this way, the temperature drop can be measured in the form of a temperature differential, where the base temperature of the heating unit and its fluctuations can be compensated for.

According to another advantageous embodiment of the disclosure it is also possible to determine the amount of evaporated liquid by means of capturing the temporal progression of the temperature drop.

BRIEF DESCRIPTION OF THE DRAWING

Below, an exemplified embodiment of the disclosure is described with the aid of a drawing. The drawing shows a schematic lateral view of an apparatus 1 for sterilizing containers F in the form of polyethylene bottles for beverages with an evaporator 2 for hydrogen peroxide in aqueous solution.

DETAILED DESCRIPTION OF DISCLOSURE

The evaporator 2 features a metal heating unit 3 with integrated electric heating cartridges 4, the power supply of which is controlled by an electronic control unit 5. Two temperature sensors T1 and T2 are connected to said control unit 5. The measurement area of the first temperature sensor T1 is arranged centrally in the heating unit 3 and thus within the actual evaporation zone, while the measurement area of the second temperature sensor T2 is arranged eccentric in the heating unit 3 and thus outside the evaporation zone. By means of the second temperature sensor T2 the control unit 5 keeps the heating unit 3 at the desired evaporation temperature of, for example, 180° C.

The evaporator 2 further comprises a pot-shaped housing 6 the bottom of which is formed by the removable, disk-shaped heating unit 3. The cover 7 of the housing 6 is also removable for cleaning purposes and carries an injector nozzle 8, the opening of which is directed downward at a right angle onto the center of the heating unit 3 and thus defines the actual evaporation zone. The injector nozzle 8 is supplied with an aqueous solution with approximately 30% of hydrogen peroxide by means of an electromagnetically actuated valve 9 and a reservoir 10. The valve 9 is actuated by the control unit 5.

A first pipeline 11 is connected laterally to the housing 6, with a boiler 12 and a blower 13, and, if necessary, with a sterile filter (not shown) and a dryer (not shown). That first pipeline 11 supplies dry, sterile air heated to a temperature of more than 100° C. laterally into the housing 6 at a certain distance from the heating unit 3. A second pipeline 14 is arranged opposite to the first pipeline 11. The air coming in though the first pipeline 11 is mixed with the hydrogen peroxide evaporated on the heating unit 3; it then leaves the housing 6 by means of the second pipeline 14 and is fed into the bottle F to be sterilized.

As has already been said, the first temperature sensor T1 is arranged centrally in the heating unit 3, a short distance from its horizontal surface forming the actual evaporating surface. It has therefore the ability to precisely capture the temperature of the evaporating surface and report it to the control unit 5. By means of the second temperature sensor T2 the control unit 5 is also informed about the base temperature of the heating unit 3 of, for example, 180° C., which it keeps constant to a large extent.

If a container F to be sterilized is connected to the second pipeline 14, the control unit 5 (for example in association with the central control of a rotating sterilization machine with several evaporators 2 and several pipelines 14) triggers a short (for example 5 seconds) opening of the valve 9 and the dropping a of a predetermined amount of hydrogen peroxide solution, for example 1 ml, onto the heating unit 3. On the evaporating surface of the heating unit 3 the hydrogen peroxide solution is instantly turned into vapor, mixed with hot air supplied through the first pipeline 11, and sucked into the second pipeline 14 from where it is fed into the bottle F. Simultaneously with the evaporation the temperature in the evaporating area drops by, for example, 20° C., which is registered by the first temperature sensor T1 and reported to the control unit 5. There, the control signal for opening the valve 9 is correlated with the temperature signal of the temperature sensor T1. If the aforementioned momentary temperature drop occurs during and/or shortly after the application of the hydrogen peroxide solution onto the heating unit 3, the evaporation process and thus the sterilization process for the given container F are deemed to be correct and recorded as such if necessary. If the aforementioned temperature drop does not occur or if it does not exceed a specified threshold value of, for example, 20° C., the evaporation process and thus the sterilization process are assessed as not sufficient or faulty and, for example, a signal is generated causing the given container F to be rejected and a warning signal to be issued.

The threshold value is advantageously associated with the base value for the heating unit temperature as measured by the temperature sensor T2 and set to a temperature differential of, for example, 20° C., so that fluctuations in the base temperature of the heating unit 3 are automatically compensated for.

The duration of the aforementioned temperature drop is relatively short because the evaporation heat is immediately compensated for by the heat supplied to the evaporator 2 by the heating elements 4. Since these parameters are essentially constant, the amount of the evaporation heat and thus the amount of the evaporated hydrogen peroxide can be determined based on the temporal progression of the temperature drop and recorded, if necessary. This is advantageous insofar as the amount of hydrogen peroxide solution necessary for sterilizing for one bottle F is very small and thus difficult to determine by other means, for example by flow measurement. The method according to the disclosure thus allows for a simple and complete control of the evaporation process.

If the evaporation phase lasting, for example, several seconds is followed by a "quiet phase" of the heating unit 3, also lasting, for example, several seconds, with the valve 9 closed, during which, for example, the hydrogen peroxide vapor is rinsed from the bottle F, then it is possible to use a single temperature sensor T1 which is then also responsible for controlling the heating cartridge 4. It such a case the temperature sensor T1 monitors the temperature increase of the heating unit 3 during this quiet phase.

The heating unit 3 can also have a pot-like shape as shown by the dotted line in the drawing.

The invention claimed is:

1. Method for monitoring an evaporator, comprising
   applying a liquid onto a liquid application area of a heating unit and evaporating the liquid,
   capturing a temperature drop in the heating unit caused by the evaporation,
   measuring the temperature of the heating unit in the area where the liquid is applied,
   measuring the temperature of the heating unit outside of the liquid application area,
   correlating that measured outside temperature with the temperature measured in the liquid application area,
   determining whether the evaporation process of the evaporator is correct or not based on the detected temperature drop, and
   capturing the temporal progression of the temperature drop, and using that captured temporal progression to determine the amount of evaporated liquid.

2. Apparatus for monitoring an evaporator for a liquid, comprising
   a heating unit,
   an injector nozzle for the liquid to be evaporated targeted at said heating unit,
   a temperature sensor for capturing the temperature of the heating unit, the temperature sensor being arranged within the liquid application area of the heating unit to capture the temperature drop in the heating unit due to the evaporation heat,
   a second temperature sensor that is arranged outside of the liquid application area to capture the temperature of the heating unit outside of the evaporation area, and
   wherein the temperature sensor is connected to a control unit which is configured to intermittently open a valve for the injector nozzle and in the absence of a predetermined temperature drop to generate a signal with the valve open.

* * * * *